(12) United States Patent
Sun et al.

(10) Patent No.: US 11,054,407 B2
(45) Date of Patent: Jul. 6, 2021

(54) GAS LOGGING SYSTEM

(71) Applicant: JILIN UNIVERSITY, Changchun (CN)

(72) Inventors: Youhong Sun, Changchun (CN); Zhiyong Chang, Changchun (CN); Xiaohui Weng, Changchun (CN); Lili Ren, Changchun (CN); Baochang Liu, Changchun (CN); Renchu Guan, Changchun (CN); Wei Guo, Changchun (CN); Jun Xie, Changchun (CN); Ke Gao, Changchun (CN); Jianhua Lv, Changchun (CN); Wei Liu, Changchun (CN); Sunhua Deng, Changchun (CN)

(73) Assignee: JILIN UNIVERSITY, Changchun (CN)

( * ) Notice: Subject to any disclaimer, the term of this patent is extended or adjusted under 35 U.S.C. 154(b) by 250 days.

(21) Appl. No.: 16/427,135

(22) Filed: May 30, 2019

(65) Prior Publication Data

US 2019/0277826 A1 Sep. 12, 2019

Related U.S. Application Data

(63) Continuation of application No. PCT/CN2017/113812, filed on Nov. 30, 2017.

(30) Foreign Application Priority Data

May 8, 2017 (CN) .......................... 201710315936.7

(51) Int. Cl.
*G01N 33/28* (2006.01)
*B01D 19/00* (2006.01)
(Continued)

(52) U.S. Cl.
CPC ..... *G01N 33/2841* (2013.01); *B01D 19/0031* (2013.01); *E21B 21/067* (2013.01);
(Continued)

(58) Field of Classification Search
CPC .......... G01N 33/2823; G01N 33/2841; G01N 33/34; E21B 21/067; E21B 49/086; B01D 19/0031
See application file for complete search history.

(56) References Cited

U.S. PATENT DOCUMENTS 3,213,594 A * 10/1965 Long ..................... E21B 21/067
96/165
RE27,882 E * 1/1974 Burnham .............. E21B 21/067
95/248

(Continued)

FOREIGN PATENT DOCUMENTS

| CN | 101972995 A | 2/2011 |
|----|-------------|--------|
| CN | 102926746 A | 2/2013 |

(Continued)

OTHER PUBLICATIONS

The International Search Report of corresponding international application No. PCT/CN2017/113812, dated Mar. 5, 2018.
(Continued)

*Primary Examiner* — John Fitzgerald
(74) *Attorney, Agent, or Firm* — J.C. Patents

(57) ABSTRACT

The present application discloses a gas logging system, including a degasser configured to degas a sample to separate a gas to be tested; and a detector connected to the degasser and configured to receive the gas to be tested separated by the degasser and perform detection, where the degasser comprises a degassing cover, the degassing cover includes a spherical crown disk surface and a plurality of semipermeable membrane degassing units on the spherical (Continued)

crown disk surface, wherein the plurality of semipermeable membrane degassing units are arranged on the spherical crown disk surface according to the Fibonacci Spiral Rule. The gas logging system provided by the present application may improve the distribution uniformity of a drilling fluid on the degassing cover while increasing arrangement number, and reduce the impact on semipermeable membrane degassing units.

14 Claims, 17 Drawing Sheets

(51) Int. Cl.
E21B 21/06 (2006.01)
E21B 49/08 (2006.01)
G01N 1/34 (2006.01)

(52) U.S. Cl.
CPC .............. *E21B 49/086* (2013.01); *G01N 1/34* (2013.01); *G01N 33/2823* (2013.01)

(56) References Cited

U.S. PATENT DOCUMENTS

| | | | |
|---|---|---|---|
| 4,381,191 A | 4/1983 | Brand et al. | |
| 8,966,955 B2 | 3/2015 | Henderson | |
| 9,744,478 B1* | 8/2017 | Ball, IV | B01D 17/0214 |
| 2010/0326075 A1* | 12/2010 | Fong | F01K 27/00 60/650 |
| 2010/0329903 A1* | 12/2010 | Fong | F15B 1/00 417/398 |
| 2011/0023488 A1* | 2/2011 | Fong | F01K 27/00 60/659 |
| 2011/0023977 A1* | 2/2011 | Fong | F01K 25/10 137/340 |
| 2011/0115223 A1* | 5/2011 | Stahlkopf | F04B 49/22 290/7 |
| 2011/0314800 A1* | 12/2011 | Fong | F15B 15/20 60/398 |
| 2012/0019009 A1* | 1/2012 | Fong | F03D 9/28 290/1 R |

FOREIGN PATENT DOCUMENTS

| | | |
|---|---|---|
| CN | 104689715 A | 6/2015 |
| CN | 105019841 A | 11/2015 |
| CN | 105735924 A | 7/2016 |
| CN | 106474774 A | 3/2017 |
| CN | 206214833 U | 6/2017 |
| CN | 106950254 A | 7/2017 |
| JP | S54-131178 A | 10/1979 |

OTHER PUBLICATIONS

The Chinese First Examination Report of corresponding Chinese application No. 201611074676.0, dated Mar. 29, 2018.

* cited by examiner

US 11,054,407 B2

GAS LOGGING SYSTEM

CROSS-REFERENCE TO RELATED APPLICATIONS

This application is a continuation of International Application No. PCT/CN2017/113812, filed on Nov. 30, 2017, which claims priority to Chinese Patent Application No. 201611074676.0, filed on Nov. 30, 2016, and Chinese Patent Application No. 201710315936.7, filed on May 8, 2017. All of the aforementioned patent applications are hereby incorporated by reference in their entireties.

TECHNICAL FIELD

The present application relates to the field of mechanical engineering technologies and specifically relates to the field of oil and gas exploration technologies and, in particular, to a gas logging system.

BACKGROUND

A gas logging system is widely used in the field of mechanical engineering. For example, the gas logging system may timely detect downhole gas in the field such as oil and gas exploration of oil shale.

SUMMARY

An object of the present application is to provide an improved gas logging system.

In one aspect, the present application provides a gas logging system, including:

a degasser, configured to degas a sample to separate a gas to be tested;

a detector, connected to the degasser and configured to receive the gas to be tested separated by the degasser and perform detection, wherein, the degasser includes a degassing cover, the degassing cover comprises a spherical crown disk surface and a plurality of semipermeable membrane degassing units on the spherical crown disk surface, wherein the plurality of semipermeable membrane degassing units are arranged on the spherical crown disk surface according to Fibonacci Spiral Rule, and an arrangement formula thereof is:

$$\begin{cases} R = R_0 * \sqrt{1 - e^{-kn}} \\ \theta = 137.5° \; n \end{cases}$$

where R is a polar coordinate radius of a $n^{th}$ semipermeable membrane degassing unit; $R_0$ is a radius of the semipermeable membrane degassing unit; K is a leaf arrangement parameter, and is 5, 6, 7 or 8; n is a serial number of a node from a center to an outside, wherein the first node of arrangement of the semipermeable membrane degassing units is n=0, the second node is n=1, and so on; θ is an angle between a $n^{th}$ node and a $n+1^{th}$ node in a polar coordinate system.

In another aspect, the present application provides a degasser for degassing a sample to separate a gas to be tested, including:

a degassing cover including a spherical crown disk surface and a plurality of semipermeable membrane degassing units on the spherical crown disk surface, wherein the plurality of semipermeable membrane degassing units are arranged on the spherical crown disk surface according to Fibonacci Spiral Rule, and an arrangement formula thereof is:

$$\begin{cases} R = R_0 * \sqrt{1 - e^{-kn}} \\ \theta = 137.5° \; n \end{cases}$$

where R is a polar coordinate radius of a $n^{th}$ semipermeable membrane degassing unit; $R_0$ is a radius of the semipermeable membrane degassing unit; K is a leaf arrangement parameter, and is 5, 6, 7 or 8; n is a serial number of a node from a center to an outside, wherein the first node of arrangement of the semipermeable membrane degassing units is n=0, the second node is n=1, and so on; θ is an angle between a $n^{th}$ node and a $n+1^{th}$ node in a polar coordinate system.

The gas logging system provided by the present application may improve the distribution uniformity of a drilling fluid on the degassing cover while increasing arrangement number, and reduce the impact on semipermeable membrane degassing units.

Figure 1:
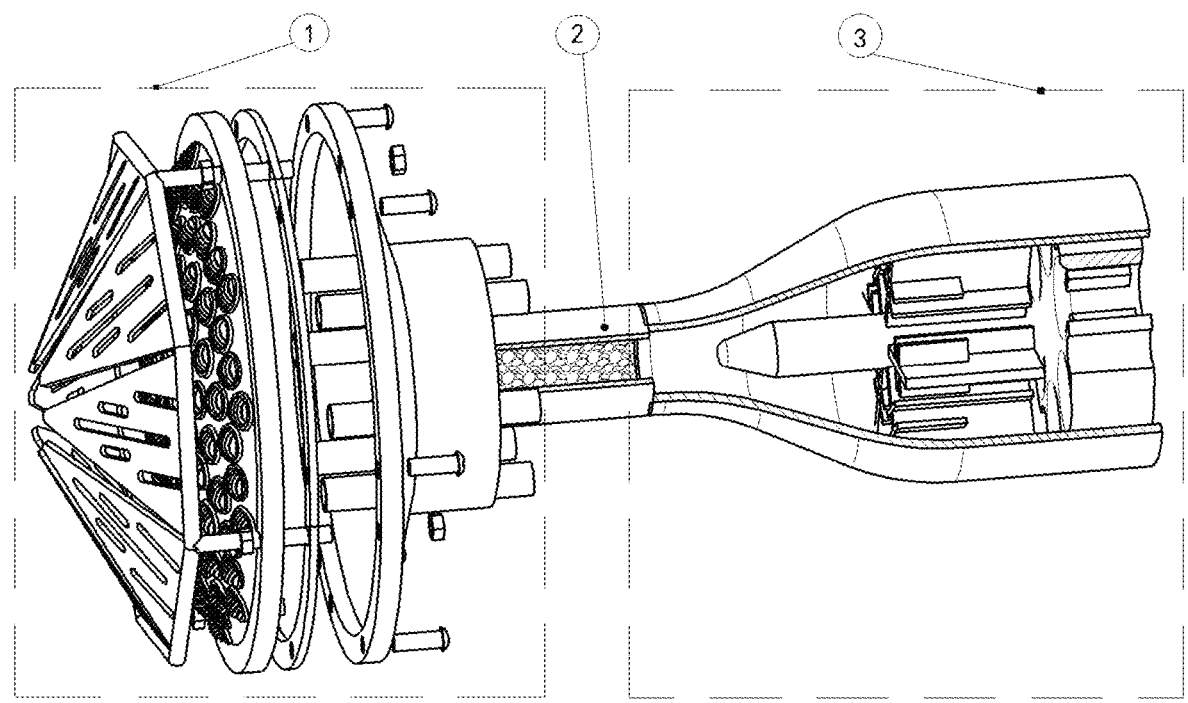
FIG. 1 is a schematic diagram of a gas logging system according to an embodiment of the present application.

Where: ① degasser, ② enrichment apparatus, ③ detector, A. steady-flow cover, B. degassing cover, C. gasket, D. rear cover, E. semipermeable membrane degassing unit, F. housing, G support column, J. baffle assembly, M. base assembly, N. sensor group, 1. adjusting nut, 2. fixing screw, 3. fixing nut, 4. elastic sheet, 5. foundation ring, 6. leg, 7. hollowed out slot I, 8. hollowed out slot II, 9. hollowed out slot III 10. hollowed out slot IV, 11. hollowed out slot V, 12. spherical crown disk surface, 13. bottom ring, 14. fixing hole I, 15. adjusting hole I, 16. toothed semipermeable membrane, 17. flexible annular base, 18. adjusting hole II, 19. fixing hole II, 20. ring table, 21. cover plate, 22. boss, 23. carrier gas input pipe, 24. fixing hole III, 25. adjusting hole III, 26. circular table, 27. mounting hole, 28. base, 29. baffle, 30. upper spoiler, 31. lower spoiler, 32. semicircular hole.

DESCRIPTION OF EMBODIMENTS

The present application will be further described in detail below with reference to the accompanying drawings and embodiments. It will be understood that the described specific embodiments herein are merely illustrative of the invention, rather than to limit the present invention. It will also be noted that, for convenience of description, only the relevant parts of the related invention are shown in the drawings.

It should be noted that the embodiments in the present application and the features in the embodiments may be combined in the case of no confliction. The present application will be described in detail below with reference to the drawings in combination with the embodiments.

Herein, directional terms such as "upper", "lower", "front", "rear", "left", "right" are intended to mean a relative position relationship between described components, not intended to limit orientations or positions of the described components.

Herein, a length unit such as "mm" is intended to mean a relative length between the described components, that is, a ratio of lengths, and not intended to limit absolute lengths of the described components, for example, it may be that a first component is 1 mm and a second component is 2 mm, and it may also be that the first component is 3 mm and the second component is 6 mm. Also, lengths indicated may have certain tolerances.

Herein, the number of each component is merely exemplary and is limiting.

A gas logging system according to an embodiment of the present application may include a degasser configured to degas a sample to separate a gas to be tested; and a detector connected to the degasser and configured to receive the gas to be tested separated by the degasser and perform detection.

In a specific embodiment shown in FIGS. 1, 2, and 3, the gas logging system may also include an enrichment apparatus ② (will be described in more detail below). That is, in the shown specific embodiment, the gas logging system according to the embodiments of the present application may include a degasser ①, an enrichment apparatus ② connected to the degasser ①, and a detector ③ connected to the enrichment apparatus ②. In, for example, an oil and gas exploration process, when the gas logging system according to the embodiments of the present application is operated, the degasser ① is used to degas (i.e. oil and gas separation) a sample (for example, a drilling fluid for detection of a downhole gas) to separate a gas to be tested. The separated gas to be tested is supplied to the enrichment apparatus ② for enrichment and desorption. The desorbed gas to be tested is supplied to the detector ③ for detection, so as to for example determine components of the gas to be tested or determine the concentration of the gas to be tested and the like. Both ends of the enrichment apparatus ② may be connected to the degasser ① and the detector ③ by screws.

The degasser ① may include a degassing cover B. As shown in FIGS. 1, 2, 9 and 10, the degassing cover B may include a spherical crown disk surface 12 and a plurality of semipermeable membrane degassing units E on the spherical crown disk surface 12. Where, the semipermeable membrane degassing units E are arranged on the spherical crown disk surface 12 according to Fibonacci Spiral Rule, and an arrangement formula thereof is:

$$\begin{cases} R = R_0 * \sqrt{1 - e^{-kn}} \\ \theta = 137.5° \; n \end{cases}$$

Where, R is a polar coordinate radius of a $n^{th}$ semipermeable membrane degassing unit; $R_0$ is a radius of the semipermeable membrane degassing unit and is 3-5 mm; K is a leaf arrangement parameter, and is 5-8; n is a serial number of a node from a center to an outside, for example the first node of arrangement of the semipermeable membrane degassing units is n=0, the second node is n=1, and so on; θ is an angle between a $n^{th}$ node and a $n+1^{th}$ node in a polar coordinate system.

The semipermeable membrane has certain separation selectivity for hydrocarbon components, and may separate oil and gas to obtain gaseous hydrocarbon components and liquid hydrocarbon components at room temperature. The semipermeable membrane has the advantages of less affected factors and being able to quantitatively evaluate the contents of oil and gas, compared with electric or pneumatic degassers.

It should also be noted that the inventors have found that the arrangement of leaves of many plants in nature conforms to strict mathematical rules, and this kind of arrangement rule is called as "leaf arrangement", such as a sunflower disk, whose seed arrangement order conforms to the Fibonacci Spiral Rule, and on one hand, this arrangement makes seeds to be arranged on the disk to the utmost extent, and on the other hand, each flower receives light more uniformly, and the stability when facing the wind may be increased. Therefore, by arranging the semipermeable membrane degassing units E on the spherical crown disk surface 12 according to the Fibonacci Spiral Rule i (i.e., seed arrangement order of sunflower disk) of the leaf arrangement theory, it is capable of improving the distribution uniformity of a drilling fluid on the degassing cover while increasing arrangement number, and reducing the impact on the semipermeable membrane degassing units E. In addition, an arc-shaped structure of the spherical crown disk surface 12 may improve pressure resistance of the degasser.

As shown in FIGS. 1, 2, 8, and 9, the degassing cover B may further include a bottom ring 13 that surrounds the spherical crown disk surface 12. The bottom ring 13 has an outer circle diameter D2 of 100 mm and an inner circle diameter D3 of 85-90 mm, and a plane circumference between the outer circle and the inner circle is evenly distributed with four adjusting holes I 15 and six fixing holes I 14, where internal threads are disposed in the four adjusting holes I 15, hole diameters of the four adjusting holes I 15 and six fixing holes I 14 are 3 mm, and the closest angle α1 between the four adjusting holes I 15 to the six fixing holes I 14 is 15°; a thickness H1 of the bottom ring 13 is 4 mm, a radius R1 of a sphere in which the spherical crown disk surface 12 is located is 90-110 mm, and a height h1 of the spherical crown disk surface 12 is 10 mm. However, it should be noted that the specific lengths, heights, quantities, and the like of the components are merely exemplary, and the scope of the present application is not limited to the specific lengths, heights, quantities, and the like of the components described as above and below.

Figure 10:
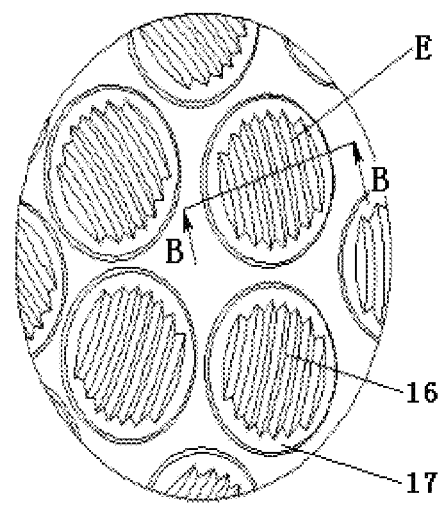
FIG. 10 is a schematic structural diagram of a semipermeable membrane degassing unit according to an embodiment of the present application.
Figure 11:
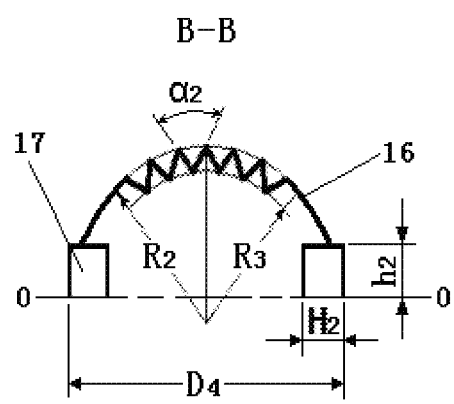
FIG. 11 is a B-B cross-sectional view of FIG. 10.

As shown in FIGS. 10 and 11, the semipermeable membrane degassing unit E may include a flexible annular base 17 and a toothed semipermeable membrane 16 within the flexible annular base 17. In specific embodiments shown in the figures, the flexible annular base 17 has an outer diameter D4 of 14 mm, a thickness H2 of 2 mm, and a height h2 of 2 mm; a central portion of a cross-sectional profile of the toothed semipermeable membrane 16 has six teeth with an angle α2 of 75°, a circle where tooth crests are has a radius R2 of 7 mm, a circle where tooth roots are has a radius R3 of 6 mm, and the toothed semipermeable membrane 16 is formed by a 180° rotation of the cross-sectional profile around an axis o-o, a bottom end of the toothed semipermeable membrane 16 is fixed to a upper end of the flexible annular base 17.

It should be noted that the inventors have found that a "skin tooth" structure on a skin surface of a shark not only reduces resistance during swimming of the shark, but also has functions of reducing microbial attachment, and decontamination and self-cleaning, and an unique form of flow field is formed on its skin surface by changing an angle of placoid scale to change an inflow angle of the "skin tooth", which provides a bionic reference for the design of the semipermeable membrane degassing units of the present application. Therefore, fixing the toothed semipermeable membrane 16 to the flexible annular base 17 may realize the function of changing an angle-of-attack of the semipermeable membrane. In addition, a surface of the toothed semipermeable membrane 16 cooperating with the flexible annular base 17 will also form an unique form of flow field, so that fine drilling fluid particles are not easily deposited, thereby maintaining cleanliness of the surface of the toothed semipermeable membrane and ensuring degassing efficiency and accuracy of an oil and gas separation unit.

Figure 2:
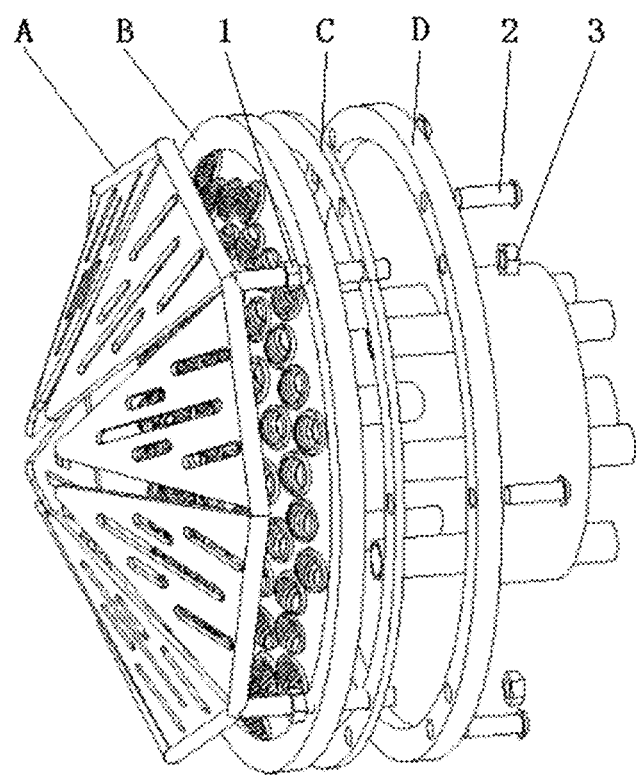
FIG. 2 is a schematic diagram of a degasser according to an embodiment of the present application.

As shown in FIGS. 1 and 2, in this embodiment, the degasser ① may further include steady-flow cover A disposed before the degassing cover B. The steady-flow cover A includes a plurality of elastic sheets, and the elastic sheets are provided with hollowed out slots, where the elastic sheets are the same isosceles triangles, and extending directions of the hollowed out slots are substantially perpendicular to bottom edges of corresponding isosceles triangles. The steady-flow cover A according to the present application may change an angle between it and an outer ring plane by the impact of a drilling fluid, so as to change a passing area of the drilling fluid, thereby realizing passive control of flow rate of the drilling fluid passing through the degassing cover to make it more stable and uniform, thus buffering the impact of the drilling fluid on the semipermeable membrane degassing units. In some specific embodiments, an apex angle of the elastic sheets may be provided with a chamfer having a certain radius.

Figure 5:
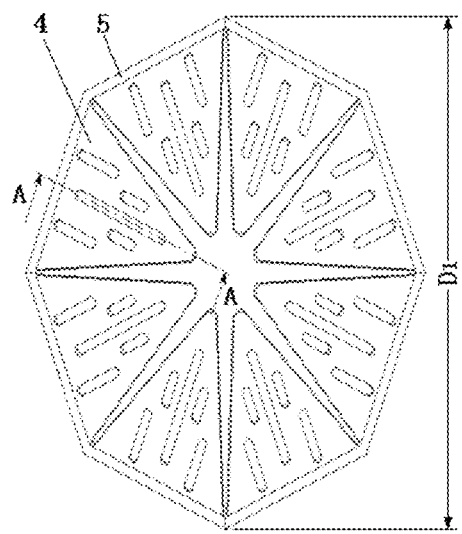
FIG. 5 is a top view of a steady-flow cover according to an embodiment of the present application.
Figure 7:
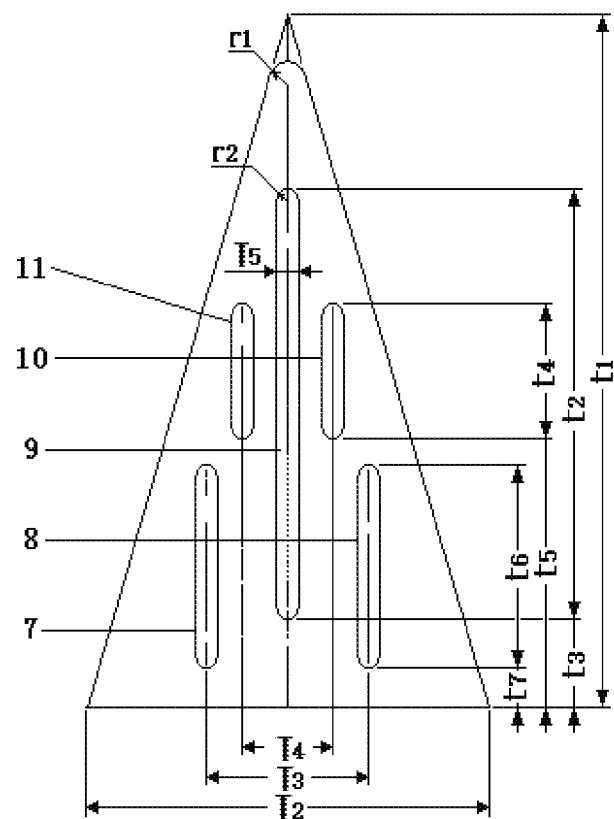
FIG. 7 is a schematic structural diagram of an elastic sheet of a steady-flow cover according to an embodiment of the present application.
Figure 8:
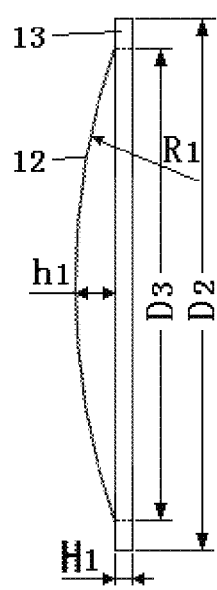
FIG. 8 is a side view of a degassing cover according to an embodiment of the present application.
Figure 9:
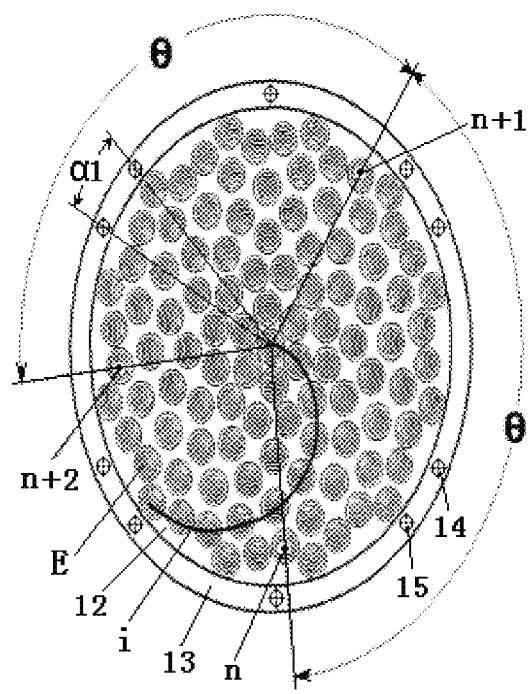
FIG. 9 is a schematic plan diagram of a degassing cover according to an embodiment of the present application.

In a specific embodiment shown in FIGS. 5 and 7, the steady-flow cover A may include eight elastic sheets 4, a foundation ring 5, and four legs 6, where the eight elastic sheets 4 are all the same isosceles triangles with a bottom side length T2 of 35 mm and a height t1 of 40 mm, an apex angle is provided with a chamfer with a radius r1 of 1.5 mm; and the elastic sheets 4 are provided with hollowed out slots I 7, hollowed out slots II 8, hollowed out slots III 9, hollowed out slots IV 10 and hollowed out slots V 11, with a width T5 of 2-3 mm. Two ends of the hollowed out slots I 7, hollowed out slots II 8, hollowed out slots III 9, hollowed out slots IV 10 and hollowed out slots V 11 are provided with arcs having a radius r2 of 1-1.5 mm; longitudinal axes of the hollowed out slots III 9 coincide with the mid-perpendicular lines of the bottom edges of the isosceles triangles; the hollowed out slots V 11, hollowed out slots I 7, and hollowed out slots IV 10, hollowed out slots II 8 are symmetrically disposed on both sides of the hollowed out slots III 9; the hollowed out slots V 11 and the hollowed out slots IV 10 both have a length t4 of 8-10 mm, longitudinal axis distances T4 between the hollowed out slots V 11 and hollowed out slots IV 10 are 8-10 mm; the hollowed out slots I 7 and hollowed out slots II 8 both have a length t6 of 12-14 mm, and longitudinal axis distances T3 between the hollowed out slots I 7 and the hollowed out slots II 8 are 14-16 mm, the hollowed out slots III 9 have a length t2 of 27-29 mm, distances t3 between bottom ends of the hollowed out slots III 9 and the bottom edges of the isosceles triangles are 4 mm; distances t7 between bottom ends of the hollowed out slots I 7 and the hollowed out slots II 8 and the bottom edges of the isosceles triangles are 2 mm; the distances t5 between bottom ends of the hollowed out slots IV 10 and the hollowed out slots V 11 and the bottom edges of the isosceles triangles are 15 mm.

Figure 6:
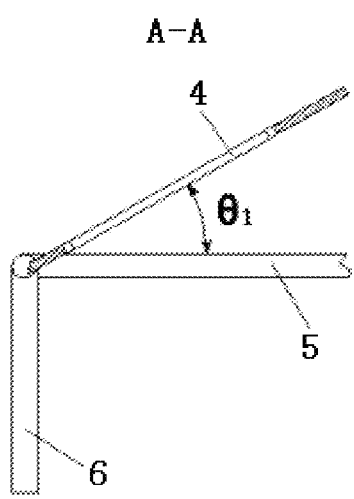
FIG. 6 is a A-A cross-sectional view of FIG. 5.

As shown in FIGS. 5 and 6, the foundation ring 5 is a regular octagon, and a circumscribed circle diameter D1 of the regular octagon is 100 mm; the bottom edges of the isosceles triangles of the eight elastic sheets 4 are fixed to sides of the regular octagon of the foundation ring 5; angles θ1 between the elastic sheets 4 and a plane of the foundation ring 5 are 30°, and the elastic modulus of each elastic sheet is 260 N/m-500 N/m.

Figure 4:
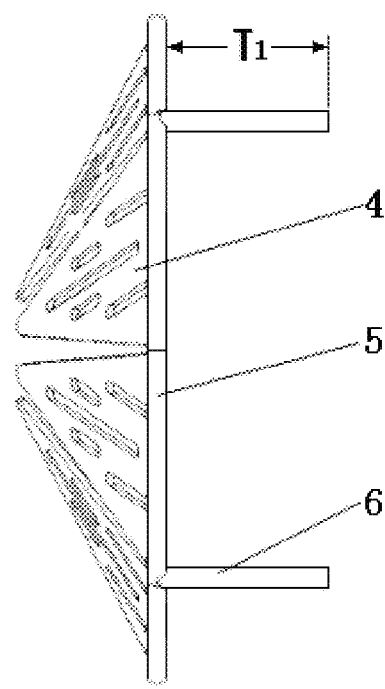
FIG. 4 is a side view of a steady-flow cover according to an embodiment of the present application.

As shown in FIG. 4, the leg 6 has a length T1 of 24 mm, and the four legs 6 are all provided with threads. Left ends of the four legs 6 are evenly distributed and fixed to four top ends of the regular octagon of the foundation ring 5.

As shown in FIGS. 1 and 2, in the present embodiment, the degasser ① may further include a gasket C connected to the degassing cover B, a rear cover D connected to the gasket C, four adjusting nuts 1, six fixing screws 2 and four fixing nuts 3. The steady-flow cover A, the four adjusting nuts 1, the degassing cover B, the gasket C, the rear cover D, and the four fixing nuts 3 are arranged in sequence from left to right, where the four adjusting nuts 1 are respectively screwed to middle portions of the four legs 6 of the steady-flow cover A, right portions of the four legs 6 of the steady-flow cover A respectively pass through four adjusting holes I 15 in the degassing cover B, four adjusting holes II 18 in the gasket C, and four adjusting holes III 26 in the rear cover D; right ends of the four legs 6 are respectively in threaded connection with the four fixing nuts 3; the six fixing screws 2 pass through the six fixing holes III 25 of the rear cover D, the six fixing holes II 19 of the gasket C from right to left respectively to screwed to the six fixing holes I 14 in the degassing cover B, thus fixing the degassing cover B, the gasket C and the rear cover D as a whole.

Figure 12:
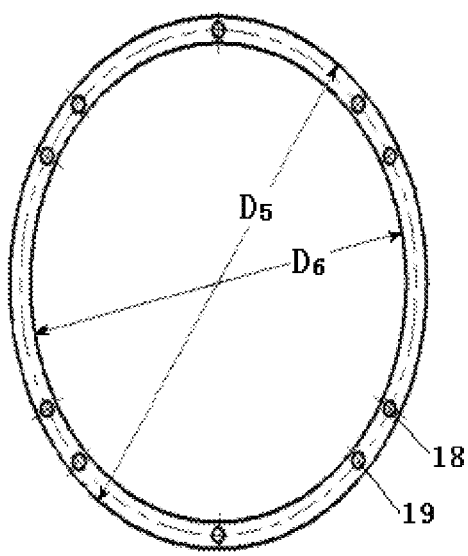
FIG. 12 is a schematic structural diagram of a gasket according to an embodiment of the present application.

As shown in FIG. 12, the gasket C has an outer diameter D5 of 100 mm, an inner diameter D6 of 90 mm and a thickness of 2 mm, and a circumference having a diameter of 95 mm of the gasket C is evenly distributed with four adjusting holes II 18 and six fixing holes II 19, and the hole diameters and hole site distribution of the four adjusting hole II 18 and the six fixing holes II 19 are the same as those of the four adjusting holes I 15 and the six fixing holes I 14 in the degassing cover B.

Figure 13:
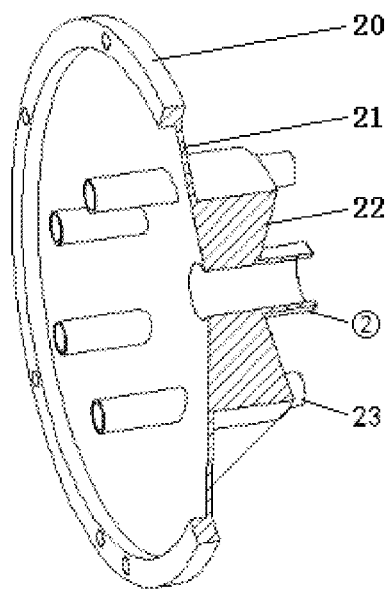
FIG. 13 is a perspective view of a rear cover according to an embodiment of the present application.
Figure 14:
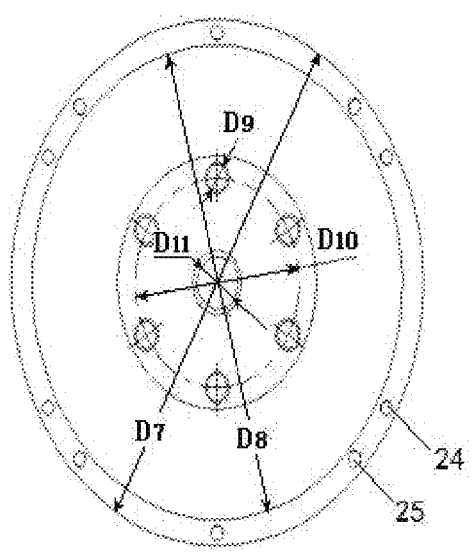
FIG. 14 is a front view of a rear cover according to an embodiment of the present application.
Figure 15:
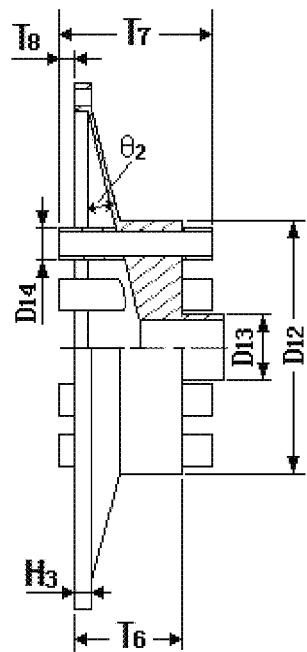
FIG. 15 is a schematic structural diagram of a rear cover according to an embodiment of the present application.
Figure 16:
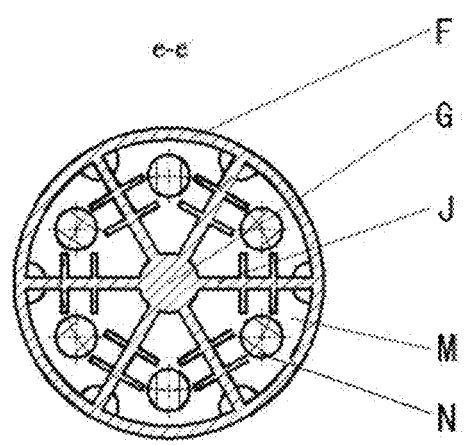
FIG. 16 is a schematic e-e cross-sectional view of FIG. 3.

As shown in FIGS. 13, 14, and 15, the rear cover D is a revolving body, and includes a ring table 20, a cover plate 21, a boss 22, and six carrier gas input pipes 23, where the ring table 20 has an outer circle diameter D7 of 100 mm, an inner circle diameter D8 of 85-90 mm, and a thickness H3 of 4 mm, and a plane between the outer circle and the inner circle of the ring table 20 is evenly distributed with four adjusting holes III 25 and six fixing hole III 24, and hole diameters and hole site distribution of the four adjusting holes III 25 and the six fixing holes III 24 are the same as those of the four adjusting holes I 15 and the six fixing holes I 14 in the degassing cover B.

As shown in FIGS. 14 and 15, an angle θ2 between the cover plate 21 and a vertical plane of the ring table 20 is 20°; a left end of the cover plate 21 is fixed to an inner ring of the ring table 20, and a right end of the cover plate 21 is fixed to a bottom end of the boss 22. The boss 22 is cylindrical and has an outer diameter D12 of 50 mm, a center of the boss 22 is in screwed connection with the enrichment apparatus ②, and six carrier gas input pipes 24 are evenly distributed on a circumference having a diameter D10 of 50 mm in the boss 22. A distance T6 between a right end surface of the boss 22 and the vertical plane of a left end of the ring table 20 is 25 mm; the carrier gas input pipe 23 has an inner diameter D9 of 5 mm, an outer diameter D14 of 7-9 mm, and a length T7 of 32-36 mm. A length T8 of a left end of the carrier gas input pipe 23 protruding from a vertical plane of the left end of the ring table 20 is 4 mm.

It will be understood by persons of ordinary skill in the art that the number of the four adjusting nuts 1, the six fixing screws 2, and the four fixing nuts 3 in the above specific embodiments may be changed, and they may also be replaced with other technical means.

In embodiments shown in the present application, the enrichment apparatus ② may be, for example, a tubular enrichment apparatus, and the enrichment apparatus ② may have an outer diameter D13 of 24 mm, a wall thickness of 4 mm, and a length of 60 mm, and is internally filled with a target gas adsorbent.

The enrichment apparatus ° enriches gases by an adsorbent distributed in a gas path (adsorbing a target gas and a thermal desorption released gas in a mixed gas flow), which may increase transient concentration of the target gas, thereby increasing recognition limit and sensitivity of the target gas.

Figure 17:
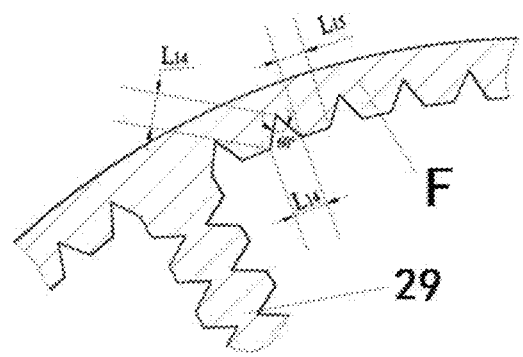
FIG. 17 is a schematic structural diagram of an inner wall groove according to an embodiment of the present application.

The detector ③ may include a housing F; a sensor group N disposed in the housing F, where an inner wall of the housing F is provided with V-shaped grooves (imitating shark skin) that are arranged along a gas flow direction (for example, as shown in FIG. 17).

It should be noted that the inventors have found that a shark skin has a V-shaped micro-groove structure arranged in a flow direction, which changes fluid structure of a fluid boundary layer at the shark body surface, and may effectively delay or suppress the conversion of a turbulent flow, thereby effectively reducing fluid resistance on the shark when the shark moves. Therefore, by arranging the V-shaped grooves in the inner wall of the housing F along the gas flow direction, the conversion of gas turbulence may be suppressed, the resistance of the inner wall of a bionic cavity on a gas to be texted may be reduced, making the gas to be tested flows in a more stable manner, thereby reducing the vibration of an instrument.

In an embodiment shown in FIG. 3 and FIGS. 19-24, the detector ③ may include a housing F having a substantially bottle shape, a thin mouth of the "bottle" is connected to the enrichment apparatus ②; a base assembly M disposed in the housing F, a base 29 of the base assembly M is fixed to a rear end of the housing F, and a circular table 26 is formed on the base 29; a support column and a top circle of the circular table (also referred to as a half-cone table) 26 in the base assembly M is fixed to a right end of the support column G; a baffle assembly J having a plurality of baffle members, where outer ends of the baffle members are fixed to the inner wall of a rear portion of the housing F, and inner ends of the baffle member are fixed to a cylindrical surface of a cylindrical body of the support column G, each of the baffle members comprises a baffle 29, an upper spoiler 30 and a lower spoiler 31, the upper spoiler 30 is fixed to a upper portion of the baffle 29, the lower spoiler 31 is fixed to a lower portion of the baffle 29, a length ratio of the upper spoiler 30 and the lower spoiler 31 is 1:2; and a sensor group N comprising a plurality of sensors, which are disposed in mounting holes 27 on the base 29 of the base assembly M. In some embodiments, a plurality of sensors are disposed at sites corresponding to the baffle members.

It should be noted that the inventors found that pig's sense of smell is very sensitive. The shape of a pig's nasal cavity is anterior small and posterior big, and a ratio of cross-sectional diameters of the anterior and posterior nasal cavities is about 2, and a nasal septum in the pig's nasal cavity separates the nasal cavity, and at the same time, the pig's nasal cavity has a turbinate bone which separates a nasal flow channel into different portions. Studies have shown that the turbinate bone may perturb and drain gas flow in the pig's nasal cavity, allowing gas to quickly reach to an olfactory zone of the pig's nose. At the same time, due to the change in the structure of a posterior segment of the turbinate bone of the pig's nasal cavity, odor molecular concentration in the olfactory zone is higher than other zones, thereby improving the pig's olfactory ability. The detector ③ of the above embodiment of the present application is made by imitating the turbinate bone structure of the pig's nasal cavity, and therefore, it may guide a gas to be tested to quickly pass through a non-detecting zone in the cavity of the housing.

Figure 3:
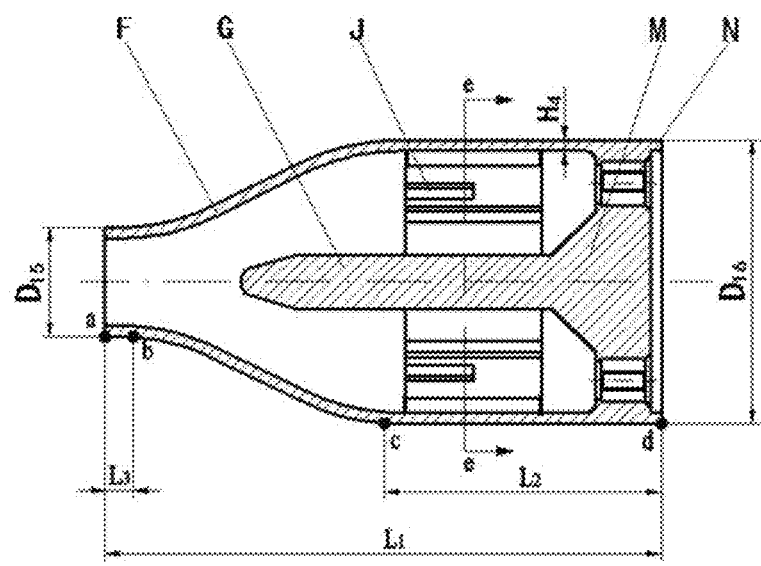
FIG. 3 is a schematic cross-sectional structural diagram of a detector according to an embodiment of the present application.

In a specific embodiment, as shown in FIG. 3, the housing F is formed by a 360° rotation of a front section ab straight line, a middle section bc curve, and a rear section cd straight line along a longitudinal axis of the housing F, and the housing F has a wall thickness H4 of 2-4 mm; a total length L1 of 200-204 mm, where a front section length L3 is 4-8 mm, and a front section outer diameter D15 is 40-44 mm, a mathematical expression for the middle section bc curve is: when it is provided that the longitudinal axis of the housing F is as a x-axis, a rightward direction is as a positive direction of the x-axis, an intersection point of the longitudinal axis of the housing F and a left end surface of the housing F is as an origin point, a y-axis is the one that goes through the origin point and is perpendicular to the x-axis, and a upward direction is as a positive direction of the y-axis, the expression is:

$$Y=8\times10^{-5}X^3-0.0134X^2+0.2323X-21.36 (4\leq X\leq 112)$$

In some embodiments, an inclined surface of the circular table 26 is provided with annular grooves. In a specific embodiment, one corner of a bottommost groove of the inclined surface of the circular table 26 is in contact with a left end surface of the base 28.

Due to the interaction of the upper spoiler, the lower spoiler and the annular grooves, the gas to be tested close to the sensor is perturbed, making the flow rate of the gas reaching to a surface of the sensor lowered, and the turbulivity of the gas to be tested increased, which not only increases a contacting time between the gas to be tested and the sensor surface, but also make the gas contact with the sensor surface more fully, so that the detection by the sensor is more stable and accurate, improving performances of the detector.

In a specific embodiment shown in Figures, a rear section length L2 is 92-96 mm, and a rear section outer diameter D1 is 100-104 mm; as shown in FIG. 17, the inner wall of the rear section cd of the housing F is provided with V-shaped grooves along the longitudinal axis direction of the housing F, one corner of a groove near the baffle 29 is just in contact with an outer surface of the baffle 29, a cross-section of the V-shaped groove is an equilateral triangle with a side length L14 of 2-3 mm, a distance L15 between adjacent V-shaped grooves is 1.5-2.4 mm.

Figure 18:
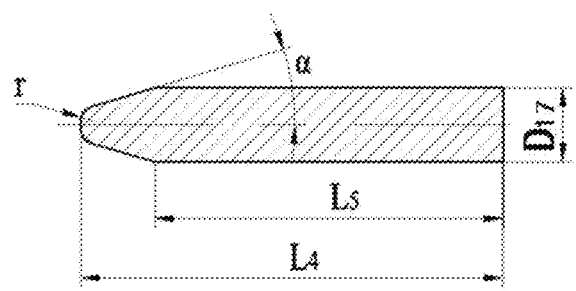
FIG. 18 is a schematic structural diagram of a support column according to an embodiment of the present application.

As shown in FIG. 18, a right portion of the support column G is a cylinder, the cylinder has a diameter D17 of 8-12 mm, a length L5 of 108-112 mm; the support column has a total length L4 of 128-136 mm, and a left end of the support column G is provided with a chamfer having a radius r of 4-6 mm, a cone is between the chamfer and the cylinder of the support column and has an angle α of 7° between generatrix thereof and a central axis.

Figure 19:
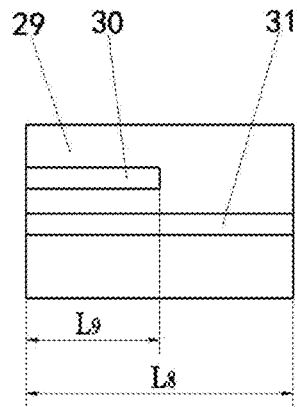
FIG. 19 is a structural front view of a spoiler according to an embodiment of the present application.
Figure 20:
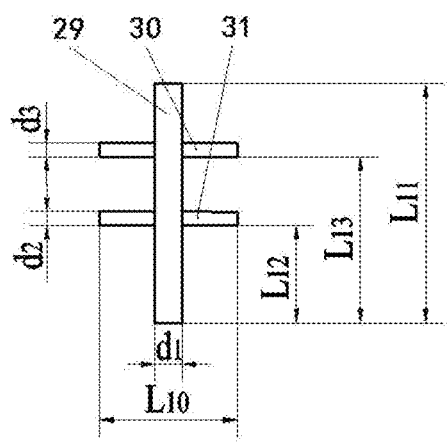
FIG. 20 is a structural side view of a spoiler according to an embodiment of the present application.

As shown in FIGS. 19 and 20, the baffle assembly J includes six identical baffle members, each of the baffle members is composed of a baffle 29, an upper spoiler 30 and a lower spoiler 31, and the baffle 29, the upper spoiler 30 and the lower spoiler 31 are all rectangles, where the baffle and the lower spoiler have a length L8 of 48-52 mm, the baffle has a height L11 of 32-36 mm and a thickness d1 of 3-5 mm, the upper spoiler 30 has a length L9 of 20-24 mm, the upper spoiler 30 and the lower spoiler 31 have a width L10 of 16-20 mm, the upper spoiler 30 has a thickness d3 of 2-3 mm, and the lower spoiler 31 has a thickness d2 of 2-3 mm; the upper spoiler 30 is fixed to an upper portion of the baffle 29, and both of them are perpendicular to each other in their width directions, and a distance L13 between a lower surface of the upper spoiler 30 and a bottom end of the baffle 29 is 20-24 mm; the lower spoiler 31 is fixed to a lower portion of the baffle 29, and both of them are perpendicular to each other in their width directions, and a distance L12 between a lower surface of the lower spoiler 31 and a bottom end of the baffle 29 is 8-10 mm.

Figure 21:
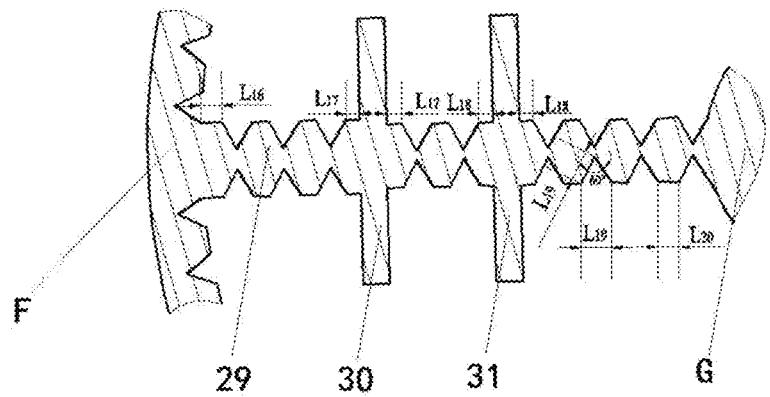
FIG. 21 is a structural diagram of a groove of a baffle according to an embodiment of the present application.

As shown in FIG. 21, left and right surfaces of the baffle 29 are provided with V-shaped grooves along a lengthwise direction of the baffle 29, and a distance L16 between a vertex of the first groove and the inner wall at a top end of the baffle 29 is 1.6-2 mm. A distance L17 between a vertex of a groove on both sides of the upper spoiler 30 and a surface of the upper spoiler 30 is 1.4-1.8 mm, and a distance L18 between a vertex of a groove on both sides of the lower spoiler 31 and a surface of the lower spoiler 31 is 1.4-1.8 mm, one corner of the last groove at a bottom end of the baffle 29 is just in contact with the surface of the support column G, a cross-section of the V-shaped groove is an equilateral triangle having a side length L19 of 2-3 mm, a distance L20 between adjacent V-shaped grooves is 1.6-2.4 mm.

Figure 22:
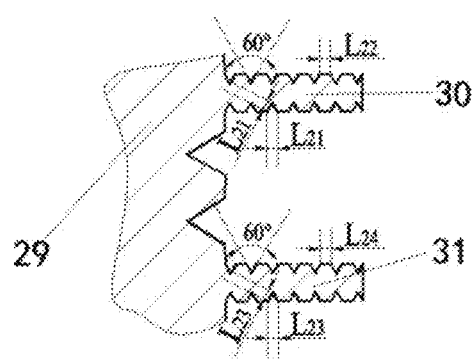
FIG. 22 is a structural diagram of a groove of a spoiler according to an embodiment of the present application.

As shown in FIG. 22, upper and lower surfaces of the upper spoiler 30 and the lower spoiler 31 are provided with V-shaped grooves along their lengthwise directions, and one corner of a groove at a bottom end of the upper spoiler 30 is just in contact with the baffle 29, one corner of a groove at a top end is just in contact with a top surface of the baffle 29, a cross-section of the V-shaped groove is an equilateral triangle with a side length L21 of 0.4-0.8 mm, and a distance L22 between adjacent V-shaped grooves is 0.4-0.6 mm, one corner of a groove at a bottom end of the lower spoiler 31 is just in contact with the baffle 29, one corner of a groove at a top end is just in contact with the top surface of the baffle 29, a cross-section of the V-shaped groove is an equilateral triangle with a side length L23 of 0.4-0.8 mm, and a distance L24 between adjacent V-shaped grooves is 0.4-0.6 mm.

Figure 23:
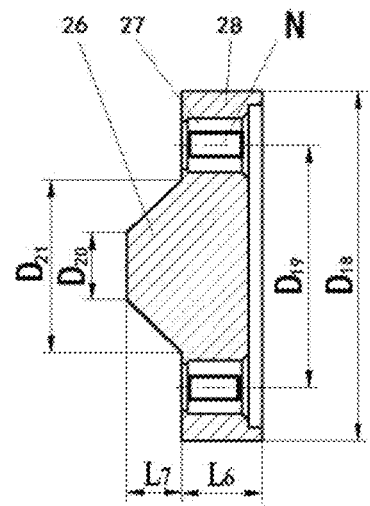
FIG. 23 is a cross-sectional view of a base assembly according to an embodiment of the present application.
Figure 24:
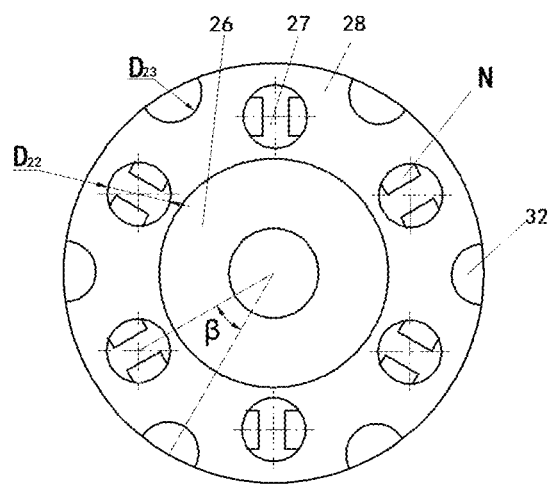
FIG. 24 is a side view of a base assembly according to an embodiment of the present application.

As shown in FIGS. 23 and 24, the base assembly M is formed by fixing the circular table 26 to the base 28, the circular table 26 has a bottom circle diameter D21 of 48-52 mm, a top circle diameter D20 of 16-20 mm, and a height L7 of 14-18 mm; the base 28 has a diameter D18 of 100-108 mm, a thickness L6 of 20-24 mm, and a middle diameter D19 of the base 28 is 72-80 mm, six mounting holes 27 are evenly distributed on the circle and have a diameter D22 of 12-16 mm, and six semicircular holes 32 are evenly distributed on an edge of the base 28 and have a diameter D23 of 12-16 mm, and angles 13 between the semicircular holes 32 and their adjacent mounting holes 27 are 30°.

Figure 25:
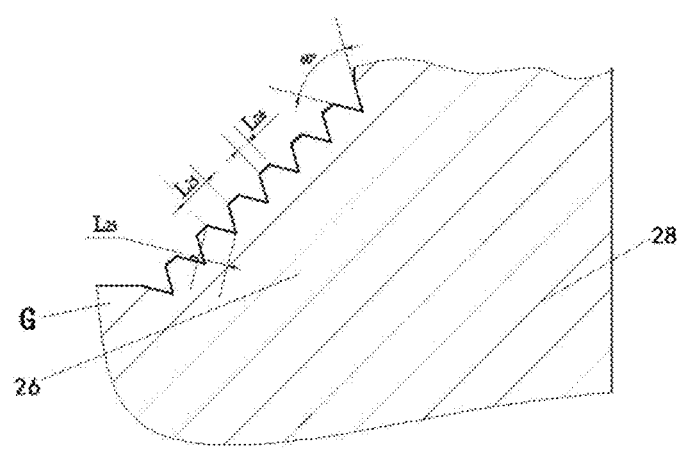
FIG. 25 is a schematic structural diagram of an annular groove according to an embodiment of the present application.

As shown in FIG. 25, an inclined surface of the circular table 26 is provided with annular grooves, one corner of a topmost groove of the inclined surface of the circular table 26 is just in contact with the surface of the support column G, and one corner of a bottommost groove of the inclined surface of the circular table 26 is just in contact with the left end surface of the base 28, and cross-sections of the annular grooves are an equilateral triangle with a side length L25 of 2-3 mm, and a distance L26 between adjacent V-shaped grooves is 1.6-2.4 mm.

The above description is only illustration of the preferred embodiments of the present invention and the technical principles applied, and should not be construed as a limitation to the present application. For example, the lengths, angles, connections, and the like described herein are merely exemplary. It should be understood by a person of ordinary skill in the art that the scope of the invention referred to in the present invention is not limited to technical solutions formed by specific combinations of the above technical features, and should also cover other technical solutions formed by arbitrary combination of the above technical features or equivalent features thereof without departing from the above inventive concept, for example, technical solutions formed by replacement of the above features with (but not limited to) technical features having similar functions disclosed in the present invention.

What is claimed is:
1. A gas logging system, comprising:
a degasser, configured to degas a sample to separate a gas to be tested;
a detector, connected to the degasser and configured to receive the gas to be tested separated by the degasser and perform detection, wherein the degasser comprises a degassing cover, the degassing cover comprises a spherical crown disk surface and a plurality of semipermeable membrane degassing units on the spherical crown disk surface, wherein the plurality of semipermeable membrane degassing units are arranged on the spherical crown disk surface according to the Fibonacci Spiral Rule, and an arrangement formula thereof is:

$$\begin{cases} R = R_0 * \sqrt{1-e^{-kn}} \\ \theta = 137.5° \; n \end{cases}$$

wherein R is a polar coordinate radius of a $n^{th}$ semipermeable membrane degassing unit; $R_0$ is a radius of the semipermeable membrane degassing unit; K is a leaf arrangement parameter, and is 5, 6, 7 or 8; n is a serial number of a node from a center to an outside, wherein the first node of the arrangement of the semipermeable membrane degassing units is n=0, the second node is n=1, and so on; θ is an angle between a $n^{th}$ node and a $n+1^{th}$ node in a polar coordinate system.

2. The system according to claim 1, wherein the degasser further comprises a steady-flow cover disposed before the degassing cover,
wherein the steady-flow cover comprises a plurality of elastic sheets, and the elastic sheets are provided with hollowed out slots, wherein the plurality of elastic sheets are the same isosceles triangles, and extending directions of the hollowed out slots are substantially perpendicular to bottom edges of corresponding isosceles triangles.

3. The system according to claim 1, further comprising:
an enrichment apparatus, disposed between the degasser and the detector, and respectively connected to the degasser and the detector, and the enrichment apparatus is configured to receive the gas to be tested separated by the degasser, perform enrichment and desorption, and supply the desorbed gas to be tested to the detector.

4. The system according to claim 1, wherein the detector comprises a housing; a sensor group disposed within the housing, wherein an inner wall of the housing is provided with V-shaped grooves that are arranged along a gas flow direction.

5. The system according to claim 1, wherein the semipermeable membrane degassing units comprise a flexible annular base and toothed semipermeable membranes on the flexible annular base.

6. The system according to claim 5, wherein each toothed semipermeable membrane comprises a plurality of teeth, tooth crests of the plurality of teeth are substantially on a circumference, tooth roots of the plurality of teeth are substantially on another circumference.

7. The system according to claim 1, wherein the detector comprises:
a housing having a substantially bottle shape;
a base assembly disposed in the housing, a base of the base assembly is fixed to a rear end of the housing, and a circular table is formed on the base;
a support column, wherein a right end of the support column is fixed to a top circle of the circular table in the base assembly;
a baffle assembly having a plurality of baffle members, wherein outer ends of the baffle members are fixed to an inner wall of a rear portion of the housing, and inner ends of the baffle members are fixed to a cylindrical surface of a cylindrical body in the support column, each of the baffle members comprises a baffle, an upper spoiler and a lower spoiler, the upper spoiler is fixed to an upper portion of the baffle, the lower spoiler is fixed to a lower portion of the baffle, a length ratio of the upper spoiler and the lower spoiler is 1:2;
a sensor group comprising a plurality of sensors, which are disposed in the base assembly.

8. The system according to claim 7, wherein the housing is formed by a 360° rotation of a front section straight line, a middle section curve, and a rear section straight line along a longitudinal axis of the housing, and when it is provided that the longitudinal axis of the housing is as a x-axis, a rightward direction is as a positive direction of the x-axis, an intersection point of the longitudinal axis of the housing and a left end surface of the housing is as an origin point, a y-axis is the one that goes through the origin point and is perpendicular to the x-axis, and a upward direction is as a positive direction of the y-axis, an expression is:

the housing $Y=8\times10^{-5}X^3-0.0134X^2+0.2323X-21.36$
($4 \leq X \leq 112$).

9. The system according to claim 7, wherein an inclined surface of the circular table is provided with annular grooves.

10. The system according to claim 9, wherein one corner of a topmost groove of the inclined surface of the circular table is in contact with a surface of the support column, and one corner of a bottommost groove of the inclined surface of the circular table is in contact with a left end surface of the base.

11. A degasser for degassing a sample to separate a gas to be tested, comprising:
a degassing cover comprising a spherical crown disk surface and a plurality of semipermeable membrane degassing units on the spherical crown disk surface, wherein the plurality of semipermeable membrane degassing units are arranged on the spherical crown disk surface according to Fibonacci Spiral Rule, and an arrangement formula thereof is:

$$\begin{cases} R = R_0 * \sqrt{1-e^{-kn}} \\ \theta = 137.5° \; n \end{cases}$$

wherein R is a polar coordinate radius of a $n^{th}$ semipermeable membrane degassing unit; $R_0$ is a radius of the semipermeable membrane degassing unit; K is a leaf arrangement parameter, and is 5, 6, 7 or 8; n is a serial number of a node from a center to an outside, wherein the first node of the arrangement of the semipermeable membrane degassing units is n=0, the second node is n=1, and so on; θ is an angle between a $n^{th}$ node and a $n+1^{th}$ node in a polar coordinate system.

12. The degasser according to claim 11, further comprising a steady-flow cover disposed before the degassing cover,
wherein the steady-flow cover comprises a plurality of elastic sheets, and the elastic sheets are provided with hollowed out slots, wherein the plurality of elastic sheets are the same isosceles triangles, and extending directions of the hollowed out slots are substantially perpendicular to bottom edges of corresponding isosceles triangles.

13. The degasser according to claim 11, wherein the semipermeable membrane degassing unit comprises a flexible annular base and toothed semipermeable membranes on the flexible annular base.

14. The degasser according to claim 13, wherein each toothed semipermeable membrane comprises a plurality of teeth, tooth crests of the plurality of teeth are substantially on a circumference, tooth roots of the plurality of teeth are substantially on another circumference.

* * * * *